United States Patent [19]

Kroker et al.

[11] Patent Number: 5,039,817
[45] Date of Patent: Aug. 13, 1991

[54] PREPARATION OF PURE N-VINYL-2-PYRROLIDONE

[75] Inventors: Ruprecht Kroker, Bobenheim-Roxheim; Guenther Mueller, Ludwigshafen; Ernst Hofmann, Lugwigshafen, all of Fed. Rep. of Germany

[73] Assignee: BASF Aktiengesellschaft, Ludwigshafen, Fed. Rep. of Germany

[21] Appl. No.: 466,456

[22] PCT Filed: Oct. 26, 1988

[86] PCT No.: PCT/EP88/00960
§ 371 Date: May 24, 1990
§ 102(e) Date: May 24, 1990

[87] PCT Pub. No.: WO89/03823
PCT Pub. Date: May 5, 1989

[30] Foreign Application Priority Data

Oct. 29, 1987 [DE] Fed. Rep. of Germany ....... 3736603

[51] Int. Cl.$^5$ ............................................ C07D 207/267
[52] U.S. Cl. ..................................... 548/543; 548/555
[58] Field of Search ................................. 548/543, 555

[56] References Cited

U.S. PATENT DOCUMENTS 4,276,215 6/1981 Hart et al. ........................... 548/555

Primary Examiner—David B. Springer
Attorney, Agent, or Firm—Keil & Weinkauf

[57] ABSTRACT

Pure N-vinyl-2-pyrrolidone is prepared by treating the crude N-vinyl-2-pyrrolidone with an acid ion exchanger.

1 Claim, No Drawings

PREPARATION OF PURE N-VINYL-2-PYRROLIDONE

The present invention relates to a process for the preparation of pure N-vinyl-2-pyrrolidone ("vinylpyrrolidone").

Vinylpyrrolidone is an important monomer for the preparation of copolymers and, especially, homopolymers, which in turn are used, for example, in medicine as plasma expanders and in cosmetics as hair fixatives. Crosslinked polyvinylpyrrolidone (polyvinylpolypyrrolidone) is used inter alia for clarifying beverages, mainly beer.

For these purposes the polymers must meet very high purity requirements, so that even the monomer must be prepared in high purity. However, the latter gives rise to considerable difficulties because the conventional synthesis from 2-pyrrolidone and acetylene produces vinylpyrrolidone containing basic substances, as is evident from the fact that a 10% by weight aqueous solution of vinylpyrrolidone, which is intrinsically neutral, has a pH of about 9 to 10.

Although vinylpyrrolidone can be purified by distillation (Ullmanns Enzyklopädie der Technischen Chemie, 4th edition, volume 23 (1983), page 611), the purifying effect achievable thereby with normal technical resources is insufficient. More extensive purification is associated with longer exposure of vinylpyrrolidone to heat, which leads to partial polymerization thereof and, consequently, considerable technical problems with distillation, to say nothing of the losses of vinylpyrrolidone.

Furthermore, DE-A 224 23 607 discloses the removal of polar compounds, including N-methylpyrrolidone, from liquid hydrocarbons using acid ion exchangers and, additionally, DE-A 11 71 435 and Chem. Abstr. volume 88, 1978, Abstract 50 675 m describe the purification of caprolactam using acid ion exchangers. However, these publications say nothing about treatment of N-vinyl-2-pyrrolidone, which is a highly sensitive chemical, with acidic resins.

The object of the present invention was therefore to obtain vinylpyrrolidone in highly pure form while avoiding the disadvantages described.

Accordingly, we have found a process for the preparation of pure N-vinyl-2-pyrrolidone, which comprises treating the crude N-vinyl-2-pyrrolidone with an acid ion exchanger.

Particularly suitable crude vinylpyrrolidone is that obtainable by reaction of pyrrolidone with acetylene in the presence of strong basic catalysts such as N-alkalimetal-pyrrolidones (Reppe process, see Ullmann loc. cit.). The nature of the basic impurities which are produced by this and are evident from an increase in the pH of aqueous vinylpyrrolidone solutions is unknown, but this is immaterial to the process according to the invention. It is advisable initially to purify by distillation the crude vinylpyrrolidone produced in the synthesis, before it is further treated in the manner according to the invention. The concentration of basic substances in the product purified in this way is about 200 to 500 ppm.

Suitable acid ion exchangers are acidified inorganic materials of this type, e.g. zeolites, but especially resins with carboxyl, sulfo or phosphono groups as acid groups. The resins which have the greatest importance in practice are crosslinked vinyl polymers because they are very chemically stable, contain or release virtually no impurities and can be regenerated many times.

Resins of this type are known under their proprietary names such as Amberlite ®, Dowex ®, Lewatit ® and Wofatit ®, with further designations providing information on the specific properties in each case.

In general, weakly acidic to moderately strongly acidic resins which contain carboxyl or sulfo groups are preferred to strongly acidic resins containing sulfo groups because strongly acidic resins may initiate polymerization of the vinylpyrrolidone.

Examples of suitable acid ion exchangers (cation exchangers) are Lewatit CNP 80 and CNP LF and Amberlite IRC-84, IRC-84 F 6, IRC-72 and IRC-50.

Since the exchanger resins are not exposed to particular thermal or chemical stress in the process according to the invention, and since they do not have to meet any specific selectivity requirements either, it is possible in principle to use any resins of this type, and even in the case of strongly acidic resins it is not difficult to adjust the contact times so that there is no danger of polymerization of the vinylpyrrolidone.

The vinylpyrrolidone can be treated with the acid ion exchangers batchwise by stirring it with the exchanger for a time, but in general the continuous procedure is advisable, in which the vinylpyrrolidone is allowed to run through an exchanger column.

Some preliminary tests can be carried out to determine how to proceed so that a 10% by weight aqueous solution of the treated vinylpyrrolidone has a pH from 7.0 to 7.5 in all cases; the initial pH depends on the origin and previous purification of the vinylpyrrolidone and is from about 9 to 11. The temperature is preferably from 10° to 50° C. In general, room temperature will be preferred as being particularly straightforward.

The purification process can also be carried out in the presence of a solvent, for example water, ethanol or isopropanol, and this is particularly suitable if further processing of the purified vinylpyrrolidone takes place in solution.

Otherwise, the process according to the invention entails no special techniques. This also applies to the regeneration of the loaded ion exchangers, so that no details of this need be given.

The basic impurities can be removed quantitatively by the treatment according to the invention, but a sufficient level of purity usually corresponds to 1 to 20 ppm of these substances and, correspondingly, to a pH of 7.0 to 7.5 of 10% by weight aqueous solution of the purified vinylpyrrolidone.

Since bases act to stabilize vinylpyrrolidone, the purified product is prone to polymerization. Thus, if it is not processed further, e.g. specifically polymerized, within a short time, it is expedient to add a few ppm of a base such as ammonia, triethylamine or N,N'-di-sec-butyl-p-phenylenediamine.

EXAMPLE 1

Crude vinylpyrrolidone which contained basic impurities corresponding to a pH of 9.6 of a 10% by weight aqueous solution was passed at 600 ml/h upwards through a column which had a height of 2 m and a width of 4 cm and which was packed to a height of 1.4 m with the swollen weakly acid ion exchanger Lewatit CNP 80.

The basic impurities were almost completely removed from the vinylpyrrolidone by this treatment.

The pH of a 10% by weight aqueous solution of the purified product was 7.14.

The capacity of the ion exchanger was exhausted after 120 h, and it was then regenerated as usual with sulfuric acid and could be used again in the same way.

EXAMPLE 2

Basic impurities were virtually completely removed from the crude vinylpyrrolidone in a similar manner to Example 1 but using Amberlite IRC-84 as weakly acid ion exchanger and passing vinylpyrrolidone through at 200 ml/h. The pH of a 10% by weight aqueous solution of the purified product was 7.12.

We claim:

1. A process for the preparation of pure N-vinyl-2-pyrrolidone, which comprises treating the crude N-vinyl-2-pyrrolidone with an acid ion exchanger.

* * * * *